US012592310B2

(12) United States Patent
Karri et al.

(10) Patent No.: US 12,592,310 B2
(45) Date of Patent: Mar. 31, 2026

(54) CHANNEL CALORIE CONSUMPTION AND NOTIFICATION USING MACHINE REASONING

(71) Applicant: International Business Machines Corporation, Armonk, NY (US)

(72) Inventors: Venkata Vara Prasad Karri, Visakhapatnam (IN); Tanvi Tayal, White Plains, NY (US); Shikhar Kwatra, San Jose, CA (US); Hemant Kumar Sivaswamy, Pune (IN)

(73) Assignee: International Business Machines Corporation, Armonk, NY (US)

( * ) Notice: Subject to any disclaimer, the term of this patent is extended or adjusted under 35 U.S.C. 154(b) by 1108 days.

(21) Appl. No.: 17/475,839

(22) Filed: Sep. 15, 2021

(65) Prior Publication Data

US 2023/0080387 A1     Mar. 16, 2023

(51) Int. Cl.
| | |
|---|---|
| *G16H 20/60* | (2018.01) |
| *A23L 33/00* | (2016.01) |
| *G01N 33/02* | (2006.01) |
| *G06N 5/04* | (2023.01) |

(52) U.S. Cl.
CPC .............. *G16H 20/60* (2018.01); *A23L 33/30* (2016.08); *G01N 33/02* (2013.01); *G06N 5/04* (2013.01)

(58) Field of Classification Search
CPC ........ G16H 20/60; A23L 33/30; G01N 33/02; G06N 5/04; G06N 20/20
See application file for complete search history.

(56) References Cited

U.S. PATENT DOCUMENTS

| | | | | |
|---|---|---|---|---|
| 5,673,691 | A | * 10/1997 | Abrams | ................. G16H 20/30 |
| | | | | 600/300 |
| 10,219,748 | B2 | 3/2019 | Terry | |
| 11,056,242 | B1 * | 7/2021 | Jain | ........................ G16H 10/60 |
| 2006/0064037 | A1 | 3/2006 | Shalon et al. | |

(Continued)

FOREIGN PATENT DOCUMENTS

| | | | | |
|---|---|---|---|---|
| CA | 2792495 | A1 * | 9/2011 | ............. G16H 20/60 |
| KR | 20140033850 | A | * 3/2014 | ........... A61B 5/4866 |

(Continued)

OTHER PUBLICATIONS

Voice enabled virtual assistant with meal recommendations (Year: 2019).*

(Continued)

*Primary Examiner* — Jay M. Patel
(74) *Attorney, Agent, or Firm* — Eric W. Chesley

(57) ABSTRACT

An approach is provided that trains an artificial intelligence (AI) system with a set of eating characteristics corresponding to a human subject. The eating characteristics include one or more eating patterns, health data, and activity data. The trained AI system generates a meal recommendation corresponding to the human subject. The meal recommendation includes a recommended meal time, and one or more food recommendations that are based upon a determined set of caloric needs pertaining to the human subject. The system automatically provides the generated meal recommendation at a time that is based on the recommended meal time using a voice-enabled virtual assistant that is accessible by the AI system.

14 Claims, 8 Drawing Sheets

(56)        References Cited

U.S. PATENT DOCUMENTS

| | | | |
|---|---|---|---|
| 2013/0158368 A1 | 6/2013 | Pacione et al. | |
| 2019/0290172 A1 | 9/2019 | Hadad | |
| 2019/0333634 A1 | 10/2019 | Vleugels | |
| 2022/0001134 A1* | 1/2022 | Tran ....................... | A61B 34/10 |
| 2022/0039358 A1* | 2/2022 | Wernimont ............ | G16H 50/20 |

FOREIGN PATENT DOCUMENTS

| | | |
|---|---|---|
| WO | 2018204763 | 11/2018 |
| WO | 2019051845 | 3/2019 |

OTHER PUBLICATIONS

Google Patent Tran, Mar. 14, 2014, KR, Dong Kyun P.*

"Maharjan, Alexa, What Should I Eat?, 2019" (Year: 2019).*

Anonymous, "Image identification of foods to calculate nutrition/ calories leveraging machine learning capabilities," ip.com, IPCOM000242182D, Jun. 23, 2015, 3 pages.

Anonymous, "Method and System for Classification and Recommendation of Food Based on How the Food is Contributing to Resting Heart Rate of Any User," ip.com, IPCOM000260844D, Dec. 27, 2019, 5 pages.

"Alzheimer's Disease: Facts & Figures," BrightFocus Foundation, 2000, 8 pages.

"2019 Alzheimer's Disease Facts and Figures," Alzheimer's Association, 2019, 1 page.

Kai et al., "Relationship between Eating Disturbance and Dementia Severity in Patients with Alzheimer's Disease," PLoS One, 2015;10(8):e0133666, Aug. 12, 2015, 13 pages.

"Managing Nutrition during Cancer and Treatment," Chemocare. com, Jan. 2021, 4 pages.

Sauer, "Malnutrition in Patients With Cancer: An Often Overlooked and Undertreated Problem," Supportive Care, Oct. 30, 2013, 8 pages.

Guedim, "Machine Learning vs Machine Reasoning: Know the Difference," Edgy, Feb. 10, 2019, 7 pages.

Buest, "Artificial Intelligence is about machine reasoning—or when machine learning is just a fancy plugin," Digital Vertices, Nov. 3, 2017, 9 pages.

"Machine Learning and Machine Reasoning for Data Analysis: The Differences You Need to Know," insideBIGDATA, May 24, 2018, 3 pages.

"What Did I Eat?" International Business Machines Corporation, Jan. 2021, 2 pages.

Wiggers, "Healbe claims its GoBe 3 wearable can track calories through the skin with up to 89 accuracy," Venture Beat, Jan. 8, 2019, 3 pages.

"Neurological disorder", Wikipedia, Aug. 2021, 7 pages, doi: https://en.wikipedia.org/wiki/Neurological_disorder.

"Thought", Wikipedia, Aug. 2021, 28 pages, doi: https://en.wikipedia.org/wiki/Thought.

S.L. Weinberg et al., "Statistics Using IBM SPSS: An Integrative Approach", Third Edition, Cambridge University Press, Mar. 2016, 1103 pages.

* cited by examiner

Information Handling System
Processor and Components

CHANNEL CALORIE CONSUMPTION AND NOTIFICATION USING MACHINE REASONING

BACKGROUND

Malnutrition is a major problem causing illness and even deaths due to multitude of factors like unawareness of what and how much to eat, forgetting when you ate last, inability to track nourishment on a daily basis etc. For instance, dementia is a broad category of brain diseases that cause a long-term and often gradual decrease in the ability to think and remember that is severe enough to affect daily functioning. For example, a high percentage of patients suffering from Alzheimer's disease display eating disturbances. Some disorders result in loss of appetite and other disorders may lead to overeating. To add to this, there is no system available which can regulate what one should eat when to overcome the ill effects of an eating disturbances. Even unintentional weight loss medical treatments, such as during cancer treatments, can lead to worse outcomes for patients when eating disturbances occur. Malnutrition and weight loss can make it harder for the patient to rebuild healthy cells between chemotherapy cycles. A high percentage of patients with certain cancers experience some form of weight loss and/or malnutrition during their cancer treatments. Unfortunately, some of these patients actually die from the effects of malnutrition rather than from the cancer itself.

SUMMARY

An approach is provided that trains an artificial intelligence (AI) system with a set of eating characteristics corresponding to a human subject. The eating characteristics include one or more eating patterns, health data, and activity data. The trained AI system generates a meal recommendation corresponding to the human subject. The meal recommendation includes a recommended meal time, and one or more food recommendations that are based upon a determined set of caloric needs pertaining to the human subject. The system automatically provides the generated meal recommendation at a time that is based on the recommended meal time using a voice-enabled virtual assistant that is accessible by the AI system.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present invention will be apparent in the non-limiting detailed description set forth below.

BRIEF DESCRIPTION OF THE DRAWINGS

The present invention may be better understood, and its numerous objects, features, and advantages made apparent to those skilled in the art by referencing the accompanying drawings, wherein.

DETAILED DESCRIPTION

Figure 1:
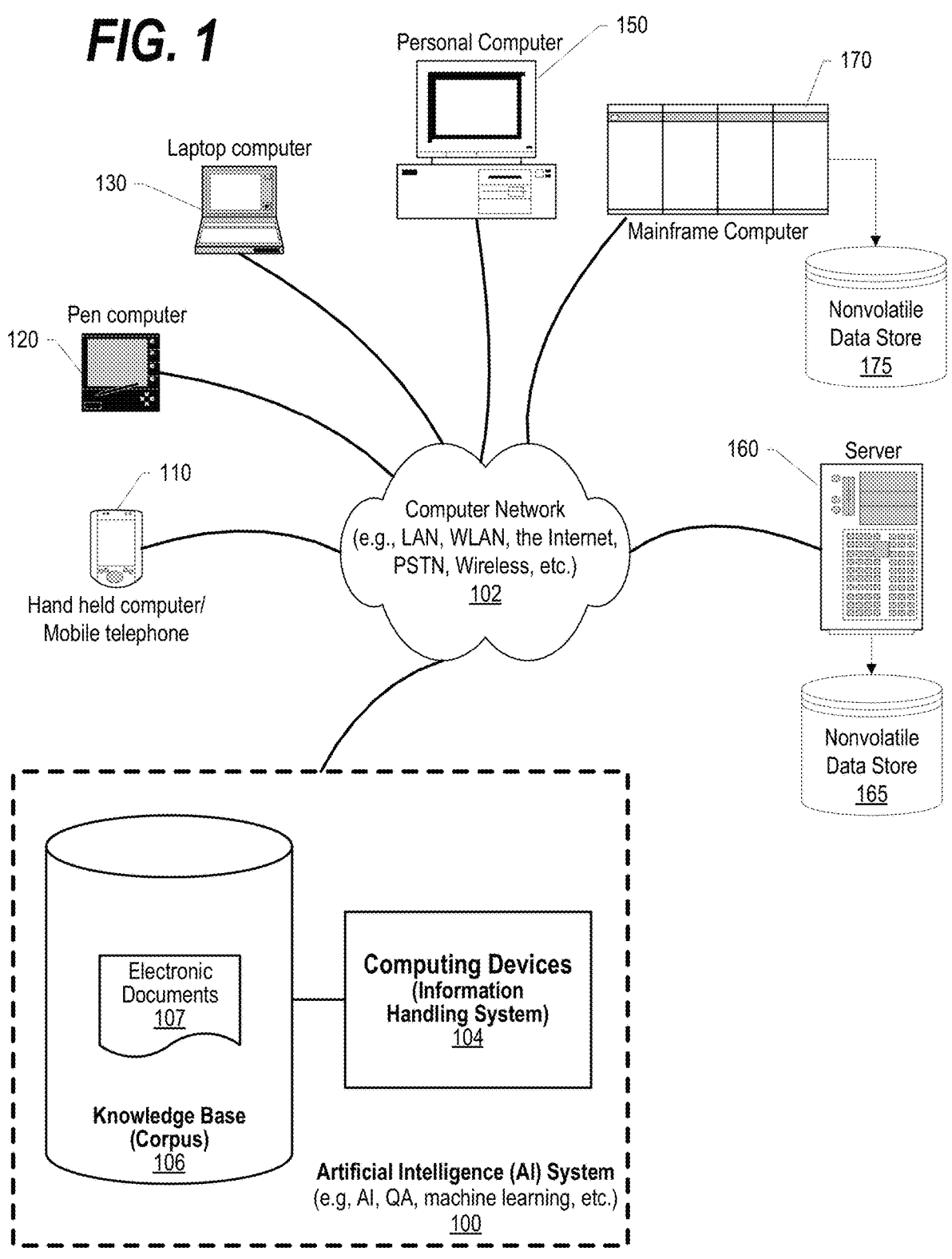
FIG. 1 depicts a network environment that includes a knowledge manager that utilizes a knowledge base.

FIGS. 1-8 describe an approach to perform a process to rationalize and channelize calorie consumption. An approach is described for activating the chat-bot virtual assistant that can interact with users using vocal commands (natural language understanding (NLU)). This provides machine reasoning to a plurality of users based on understanding a human subject's food metrics with profiling of the human subject and correlating the profile with execution of specific tasks in order to relay said information in a proactive fashion to users, such as caretakers.

The approach identifies energy consumption rate of the human subject by parameters/dimensions such as time and amount of enzyme secretion, body clock functioning, type of hiccups, last meal details—time, type and quantity etc. with the artificial intelligence (AI) system understanding the net impact on the human subject at a given point in time. The approach rationalizes calorie consumption decisions by assessing the impact of external factors such as weather, travel and body clock movements on one's body functioning, metabolism and productivity.

In one embodiment, the approach incorporates a human subject's profession which is an important part of one's lifestyle and is an important determinant of the human subject's eating patterns. If the human subject does not pay heed to the AI's verbal instructions, the system escalates the message to a user, such as a caretaker, and further initiates interaction with the caretaker regarding the human subject. The following provides an exemplary use case scenario.

Consultants by the virtue of their profession spend more than half the week in flights traveling and it is often difficult to understand when they are actually hungry. The incorrect understanding of the body clock functioning cause either under/over calorie consumption. Similarly, jobs requiring physical manpower, such as with factory floor workers, the working style regarding a typical shift body clock, calorie consumption will be very different for high productivity.

The approach utilizes AI to understand and calculate both the internal body and digestive conditions and external environments like weather, nature of job, lifestyle pattern and associated ailments for calorie intake suggestions. The approach further utilizes various data engines that are either incorporated in the AI system or have interfaces to the AI system. These data engines include an ENERGY IN data engine which estimates total calorie consumption, an ENERGY OUT data engine which calculates energy expended via activities performed, and a FACTORS data engine which factors in internal aspects like time of consumption of items, time and duration of enzyme secreted, ailments, allergies, body type and external factors like type of job role, lifestyle, body clock movements.

The net calories consumed, expended, and external environment factors and inputs from the NET TASK engine seeks user input of various factors such as the next task the human subject is about to undertake (e.g., working in office, exercising, sales visit, sleeping, etc.), the duration of the task and the time of day. The CALORIE QUOTA Calculator utilizes the AI system to predict the energy needed to undertake that basis all these factors and suggest a next meal in terms of both foods in the meal as well as the time at which the next meal is ideally consumed.

The approach utilizes an integrated virtual assistant feature of the AI system to answer questions relating to foods, and external factors such as weather and productivity. Some of this data, such as environmental factors and the human subject's activity, can be obtained using sensors that feed data to the AI system. Consider the following exemplary use case: the human subject just landed at an airport where it is currently −20 degrees outside. Within the subject's calorie limit available, the system provides him with a list of foods to choose from for a next meal, such as consuming a standard cappuccino, or an ice cream with X/Y flavors, OR 30 grams nuts etc. The system at that stance can answer which one of the choices can help the subject best boost his productivity and will stack/rank the choices available. The system further stack ranks the weather based on the subject's lifestyle and further based on the health and biological condition of the subject with meal-based options being output from the calorie quota engine of the AI system.

Once the results from calories quota engine are received, the approach takes into account the human subject's GPS location and tracks the available foods nearest the locations and suggests the food items befitting the human subject's calorie quota. In one embodiment, the approach further stack ranks them in terms of maximum productivity. The AI enabled system is agile so that when tasks are added the user undertake meal recommendations later in the day that take into account the calories IN and OUT calculated beforehand and can accordingly procure food earlier than the requisite meal time basis based on the current access to available food stores. In another embodiment, the approach auto derives meal recommendations based on the human subject's consumption data extracted from bio sensors and other similar implanted devices to make proper recommendations.

The approach can be used by individuals to stay fit and productive at any point in time. Enterprises can use the approach to plan calorie intake for human subjects being cared for by the enterprises' users, such as caretakes, and take into account the subject's profession, time of the meal, and the like. In one embodiment, the approach can be used by countries to curb problems such as malnutrition and obesity with rational outcomes. For example, the approach can predict if a person, who is about to do a strenuous job in the next couple of hours, needs additional calories for optimum performance and to meet the subject's energy needs without causing fatigue and without providing excessive calories.

In one embodiment, the approach has an IOT (Internet of Things) mechanism for user registration that first seek user inputs for details like the human subject's profession, questions determining the subject's lifestyle e.g. general food choices, acute and chronic diseases the human subject is suffering from upon registration and store in its User Engine. The user engine database is combined with a historic engine database that has details of historic information of food and wellness in general pertaining to the human subject. For example, Type A diabetes patients should not consume rice, have more water, etc., and this forms the database used for the IN data engine.

Going forward, if any of the demographic details change, such as the subject's profession, the user can edit the subject's profile at the point in time as these parameters will have a bearing in the recommendation engine. The user of the system might be the human subject if the human subject is self-managing the system provided by the approach or the user might be a caretaker if the human subject has someone else caring for the dietary needs of the subject.

The IOT device could be used as a smart watch and even be integrated in the subject's phone. The Energy Consumption engine is capable of calculating the subject's energy consumption rate by tracking the energy consumed per each activity like sleeping, walking, work/household chores, time, amount of enzyme secretion, body clock functioning, type of bodily function, and other such parameters.

Smart devices, such as wearables and smart cameras, provide human subject input regarding performed tasks. For example, if the next task of the human subject is running for 30 mins and 60 mins rest, the system predicts the time of the next meal, the calorie range that should be consumed in the meal to have maximum productivity probability, and recommended meal choices based on available foods.

The approach calculates the energy consumed by the human subject based on the last meal consumed and the subject's activities and understand the net impact (the combination of energy consumed and energy expended) on the subject's human body at a given point in time. The approach utilizes a device that is GPS enabled to help track the human subject's location and activity and to further understand the meal options falling in the subject's needed calorie range.

The IOT device utilized by the approach also stack ranks the options available on the basis the subject's lifestyle choices input to the IN data engine. The wearable portion of the system uses the data captured by the IN and FACTOR engines. The Net Calorie count—Addition of the Food Consumed so far in the day and the subtraction of energy expended while the human subject was performing various activities. The amount of enzyme secretion at that time, the type of weather, any ailment (medical) afflicting the human subject, such as diabetes, hypertension, lifestyle diseases, and the like, that impact calorie needs. The working style/job role/pattern and body clock functioning of the human subject is data further utilized by the AI component of the approach.

The AI's virtual assistant component is triggered while the system is tracking the human subject and is running in the backend receiving data from the subject's wearable sensors and smart cameras located proximate to the subject to keep track of food items ingested by the human subject and energy expended by the subject during various activities. In one embodiment, the virtual assistant is running Random forest classifier on top of image recognition module (running the YOLO algorithm—You Only Look Once algorithm capable of capturing and identifying the food items from remote cameras). In this embodiment, the Random forest classifier, the system is running the interpretability aspect in order to start interacting with the human subject and interject the human subject at the right time while the human subject is ingesting said food items.

In one embodiment, a dynamic question/answer (Q and A) is available in which the virtual assistant may provide answers with pre-stored information or directing the user to linked videos/blogs/articles based on reasoning and filters to provide highly reviewed relevant content that pertains to the human subject's food intake, eating and activity habits, and daily patterns. In this manner, the approach determines what energy consumption is optimum at that time and accordingly basis that calorie range a person can consume food. Additionally, once the human subject consumes food, this information serves as feedback and is stored under lifestyle choice, retained with the subject's historic information, and also provided to the system's energy consumption engine.

The IN data engine and energy consumption engine are dynamically refreshed by the choice of food consumed by the human subject at a particular time and impacts the results provided by the AI's virtual assistant while interacting with the user. By way of an example, a person is having a meal. The smart sensors and smart cameras (e.g., wearables sensors, etc.) measure the food intake at the time the subject is consuming a meal and provides this data to a time series analysis pattern. Using correlation metrics to associate the human subject's pattern and health metrics, the virtual assistant is initiated to interact with the user at an appropriate time before the human subject's next meal. In one embodiment, this interaction is based on a user-definable threshold. In one embodiment, if the virtual assistant interacts with the user and if the user does not pay attention to the provided instructions, the AI can escalate an intervention by another user, such as a family member, supervisor, caretaker, or the like, so that the human subject receives proper care.

FIG. 1 depicts a schematic diagram of one illustrative embodiment of artificial intelligence (AI) system 100 in a computer network 102. AI system 100 includes artificial intelligence computing device 104 (comprising one or more processors and one or more memories, and potentially any other computing device elements generally known in the art including buses, storage devices, communication interfaces, and the like) that connects AI system 100 to the computer network 102. The network 102 may include multiple computing devices 104 in communication with each other and with other devices or components via one or more wired and/or wireless data communication links, where each communication link may comprise one or more of wires, routers, switches, transmitters, receivers, or the like. AI system 100 and network 102 may enable functionality, such as question/answer (QA) generation functionality, for one or more content users. Other embodiments of AI system 100 may be used with components, systems, sub-systems, and/or devices other than those that are depicted herein.

AI system 100 maintains knowledge base 106, also known as a "corpus," which is a store of information or data that the AI system draws on to solve problems. This knowledge base includes underlying sets of facts, assumptions, models, and rules which the AI system has available in order to solve problems.

AI system 100 may be configured to receive inputs from various sources. For example, AI system 100 may receive input from the network 102, a corpus of electronic documents 107 or other data, a content creator, content users, and other possible sources of input. In one embodiment, some or all of the inputs to AI system 100 may be routed through the network 102. The various computing devices on the network 102 may include access points for content creators and content users. Some of the computing devices may include devices for a database storing the corpus of data. The network 102 may include local network connections and remote connections in various embodiments, such that artificial intelligence 100 may operate in environments of any size, including local and global, e.g., the Internet. Additionally, artificial intelligence 100 serves as a front-end system that can make available a variety of knowledge extracted from or represented in documents, network-accessible sources and/or structured data sources. In this manner, some processes populate the artificial intelligence with the artificial intelligence also including input interfaces to receive knowledge requests and respond accordingly.

In one embodiment, the content creator creates content in electronic documents 107 for use as part of a corpus of data with AI system 100. Electronic documents 107 may include any file, text, article, or source of data for use in AI system 100. Content users may access AI system 100 via a network connection or an Internet connection to the network 102, and, in one embodiment, may input questions to AI system 100 that may be answered by the content in the corpus of data. As further described below, when a process evaluates a given section of a document for semantic content, the process can use a variety of conventions to query it from the artificial intelligence.

Types of information handling systems that can utilize AI system 100 range from small handheld devices, such as handheld computer/mobile telephone 110 to large mainframe systems, such as mainframe computer 170. Examples of handheld computer 110 include personal digital assistants (PDAs), personal entertainment devices, such as MP3 players, portable televisions, and compact disc players. Other examples of information handling systems include pen, or tablet, computer 120, laptop, or notebook, computer 130, personal computer system 150, and server 160. As shown, the various information handling systems can be networked together using computer network 102. Types of computer network 102 that can be used to interconnect the various information handling systems include Local Area Networks (LANs), Wireless Local Area Networks (WLANs), the Internet, the Public Switched Telephone Network (PSTN), other wireless networks, and any other network topology that can be used to interconnect the information handling systems. Many of the information handling systems include nonvolatile data stores, such as hard drives and/or nonvolatile memory. Some of the information handling systems shown in FIG. 1 depicts separate nonvolatile data stores (server 160 utilizes nonvolatile data store 165, and mainframe computer 170 utilizes nonvolatile data store 175. The nonvolatile data store can be a component that is external to the various information handling systems or can be internal to one of the information handling systems. An illustrative example of an information handling system showing an exemplary processor and various components commonly accessed by the processor is shown in FIG. 2.

Figure 2:
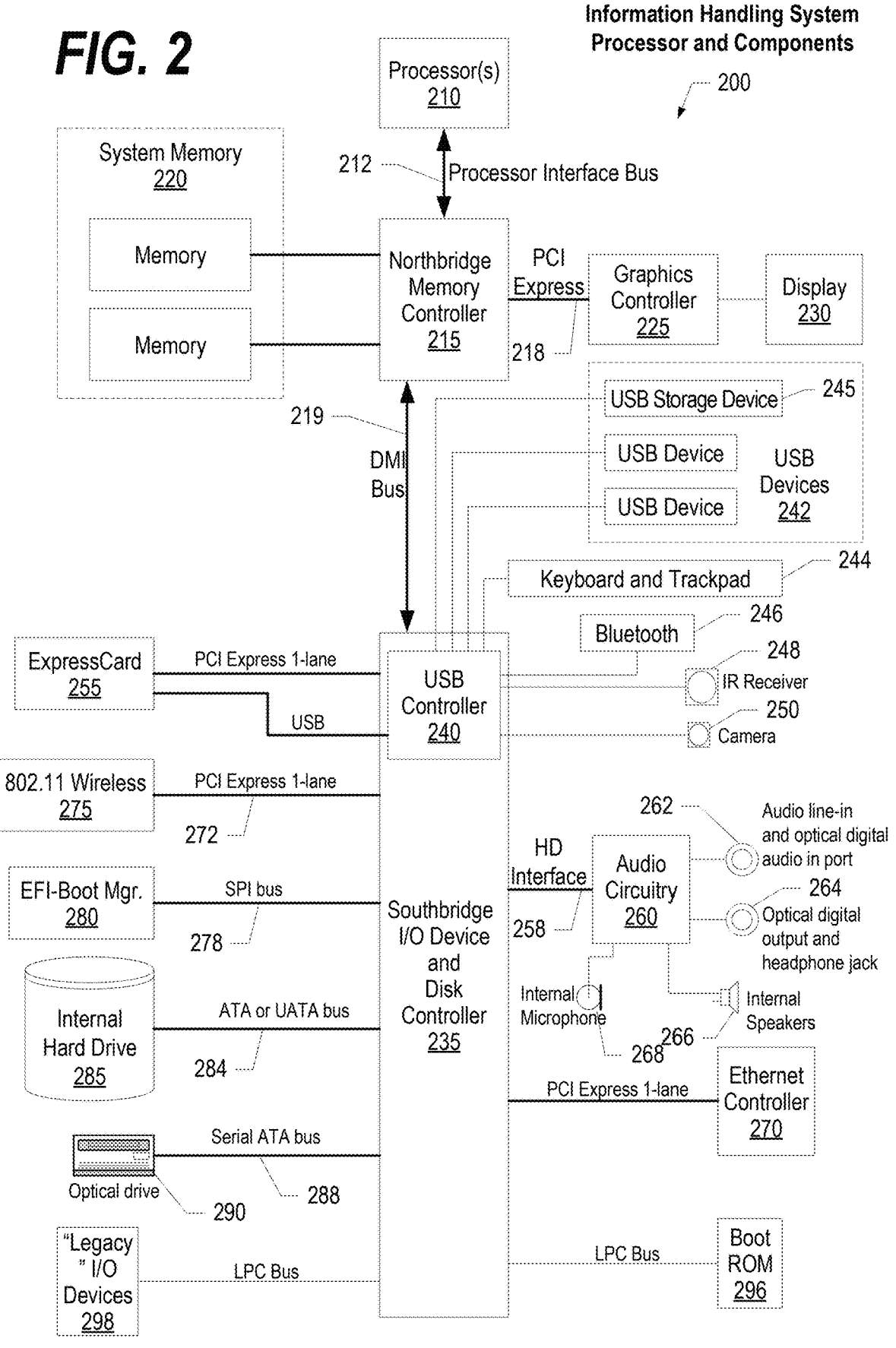
FIG. 2 is a block diagram of a processor and components of an information handling system such as those shown in FIG. 1.

FIG. 2 illustrates information handling system 200, more particularly, a processor and common components, which is a simplified example of a computer system capable of performing the computing operations described herein. Information handling system 200 includes one or more processors 210 coupled to processor interface bus 212. Processor interface bus 212 connects processors 210 to Northbridge 215, which is also known as the Memory Controller Hub (MCH). Northbridge 215 connects to system memory 220 and provides a means for processor(s) 210 to access the system memory. Graphics controller 225 also connects to Northbridge 215. In one embodiment, PCI Express bus 218 connects Northbridge 215 to graphics controller 225. Graphics controller 225 connects to display device 230, such as a computer monitor.

Northbridge 215 and Southbridge 235 connect to each other using bus 219. In one embodiment, the bus is a Direct Media Interface (DMI) bus that transfers data at high speeds in each direction between Northbridge 215 and Southbridge 235. In another embodiment, a Peripheral Component Interconnect (PCI) bus connects the Northbridge and the Southbridge. Southbridge 235, also known as the I/O Controller Hub (ICH) is a chip that generally implements capabilities that operate at slower speeds than the capabilities provided by the Northbridge. Southbridge 235 typically provides various busses used to connect various components. These busses include, for example, PCI and PCI Express busses, an ISA bus, a System Management Bus (SMBus or SMB), and/or a Low Pin Count (LPC) bus. The LPC bus often connects low-bandwidth devices, such as boot ROM 296 and "legacy" I/O devices (using a "super I/O" chip). The "legacy" I/O devices (298) can include, for example, serial and parallel ports, keyboard, mouse, and/or a floppy disk controller. Other components often included in Southbridge 235 include a Direct Memory Access (DMA) controller, aProgrammable Interrupt Controller (PIC), and a storage device controller, which connects Southbridge 235 to non-volatile storage device 285, such as a hard disk drive, using bus 284.

ExpressCard 255 is a slot that connects hot-pluggable devices to the information handling system. ExpressCard 255 supports both PCI Express and USB connectivity as it connects to Southbridge 235 using both the Universal Serial Bus (USB) the PCI Express bus. Southbridge 235 includes USB Controller 240 that provides USB connectivity to devices that connect to the USB. These devices include webcam (camera) 250, infrared (IR) receiver 248, keyboard and trackpad 244, and Bluetooth device 246, which provides for wireless personal area networks (PANs). USB Controller 240 also provides USB connectivity to other miscellaneous USB connected devices 242, such as a mouse, removable nonvolatile storage device 245, modems, network cards, ISDN connectors, fax, printers, USB hubs, and many other types of USB connected devices. While removable nonvolatile storage device 245 is shown as a USB-connected device, removable nonvolatile storage device 245 could be connected using a different interface, such as a Firewire interface, etcetera.

Wireless Local Area Network (LAN) device 275 connects to Southbridge 235 via the PCI or PCI Express bus 272. LAN device 275 typically implements one of the IEEE.802.11 standards of over-the-air modulation techniques that all use the same protocol to wireless communicate between information handling system 200 and another computer system or device. Optical storage device 290 connects to Southbridge 235 using Serial ATA (SATA) bus 288. Serial ATA adapters and devices communicate over a high-speed serial link. The Serial ATA bus also connects Southbridge 235 to other forms of storage devices, such as hard disk drives. Audio circuitry 260, such as a sound card, connects to Southbridge 235 via bus 258. Audio circuitry 260 also provides functionality such as audio line-in and optical digital audio in port 262, optical digital output and headphone jack 264, internal speakers 266, and internal microphone 268. Ethernet controller 270 connects to Southbridge 235 using a bus, such as the PCI or PCI Express bus. Ethernet controller 270 connects information handling system 200 to a computer network, such as a Local Area Network (LAN), the Internet, and other public and private computer networks.

While FIG. 2 shows one information handling system, an information handling system may take many forms, some of which are shown in FIG. 1. For example, an information handling system may take the form of a desktop, server, portable, laptop, notebook, or other form factor computer or data processing system. In addition, an information handling system may take other form factors such as a personal digital assistant (PDA), a gaming device, ATM machine, a portable telephone device, a communication device or other devices that include a processor and memory.

Figure 3:
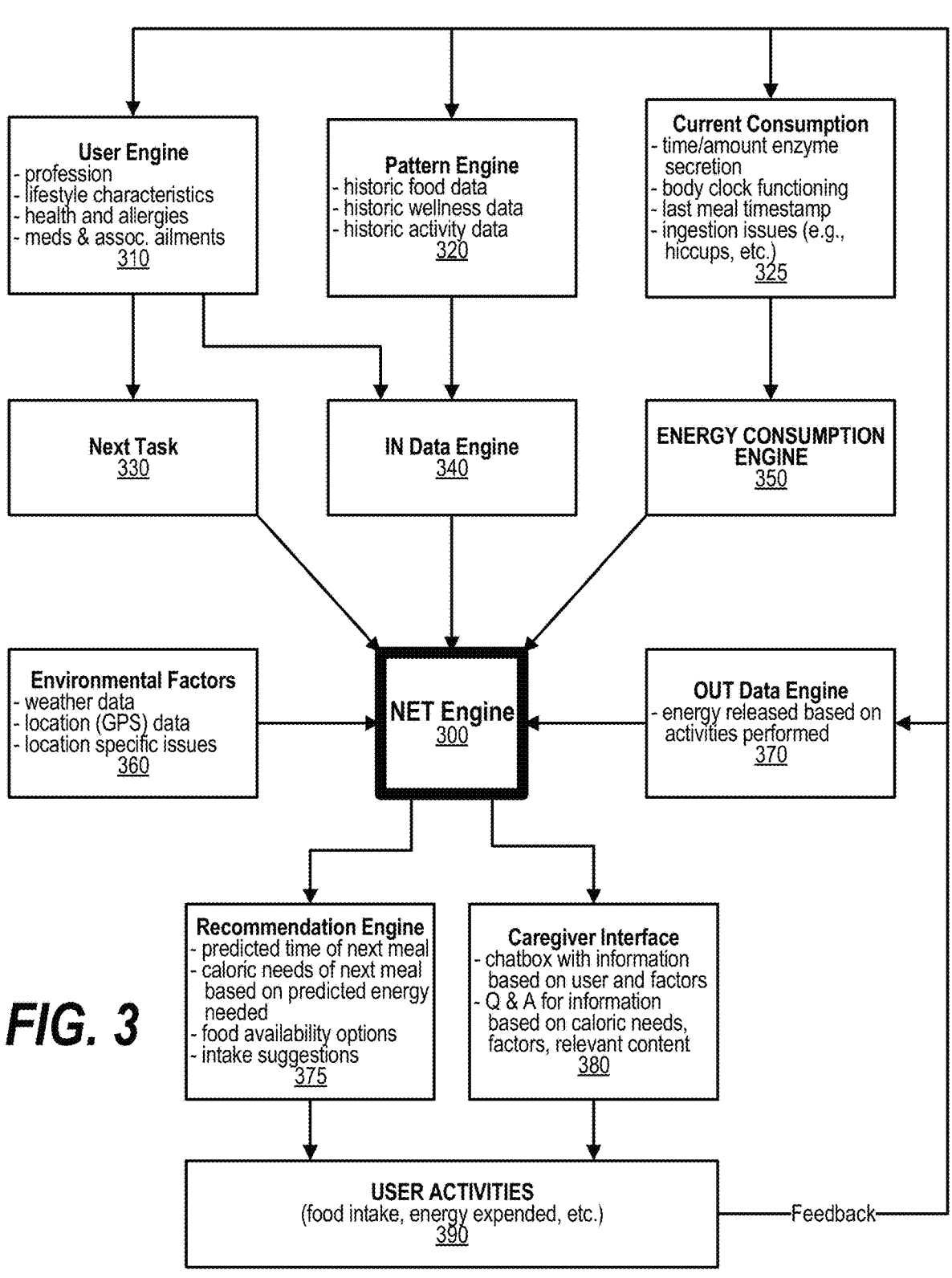
FIG. 3 is a component diagram showing various components used in a system that provides channel calorie consumption and notification using machine reasoning.

FIG. 3 is a component diagram showing various components used in a system that provides channel calorie consumption and notification using machine reasoning. NET engine 300 combines data from other engines and outputs recommendations 375 using caregiver interface 380. In one embodiment, NET engine 300 and other various engines are implemented using an artificial intelligence (AI) system.

User Engine 310 provides user data such as the human subject's profession, lifestyle characteristics (e.g., activity level, regular activities performed, etc.), the subject's health and allergy data, and the subject's medications and associated ailments (e.g., diabetes, hypertension, etc.). User engine 310 feeds its data to Next Task Engine 330 and IN Data Engine 340.

Pattern Engine 320 provides pattern data corresponding to the human subject such as the subject's historic food data, the subject's historic wellness data, and the subject's historic activity data. Current Consumption Engine 325 provides data regarding the subject's current consumption. Current consumption can include data such as the time and amount of enzyme secretion, the subject's body clock functioning, the subject's last meal timestamp and food consumed, and the subject's ingestion issues, such as hiccups, indigestion issues, etc.

Next Task 330 is identified by the AI system trained with the human subject's data discussed in FIG. 3, with the next task being a task such as a meal or an activity. IN Data Engine 340 takes inputs from User Engine 310 as well as from Pattern Engine 320 with the combined data being provided to NET Engine 300 that uses the trained AI system to identify the net impact of the inputs, factors, and outputs at a given point in time.

Energy Consumption Engine 350 uses the trained AI system to determine the amount of energy consumed by the user from the data provided by Current Consumption engine 325. Environmental Factors Engine 360 gathers the current weather data at the human subject's current geographic location (obtained using GPS sensors), as well as any location specific issues.

OUT Data Engine 370 determines, using the trained AI system, the amount of energy released by the human subject based on activities performed by the subject (e.g., running, walking, eating, sitting, sleeping, etc.).

NET Engine 300 uses the trained AI to provide outputs to Recommendations Engine 375 with such recommendations including the predicted time of the human subject's next meal, the caloric needs of next meal based on the predicted amount of energy needed by the subject, and the food availability options based on available food stores. NET Engine 300 further outputs caregiver instructions to Caregiver Interface 380 which includes virtual assistant technology accessible or incorporated into the AI system. The caregiver interface includes a verbal "chat box" with information based on the human subject and factors identified by the AI system. The interface also provides a question/answer (Q&A) interface to provide information based on caloric needs, factors, and other relevant content.

User Activities 390 are activities performed by the human subject with, in some cases, coordination being provided by a user, such as a caretaker. User activities can include items such as food intake by the subject, energy expended by the subject, and the like. This data is used in a feedback loop to engines such as OUT Data Engine 370, Current Consumption Engine 325, Pattern Engine 320, and User Engine 310.

This data is also used to continually train the AI system regarding the human subject's food consumption and activities so that the AI system can adapt to changes in the environment and better predict the human subject's activities and meal requirements.

Figure 4:
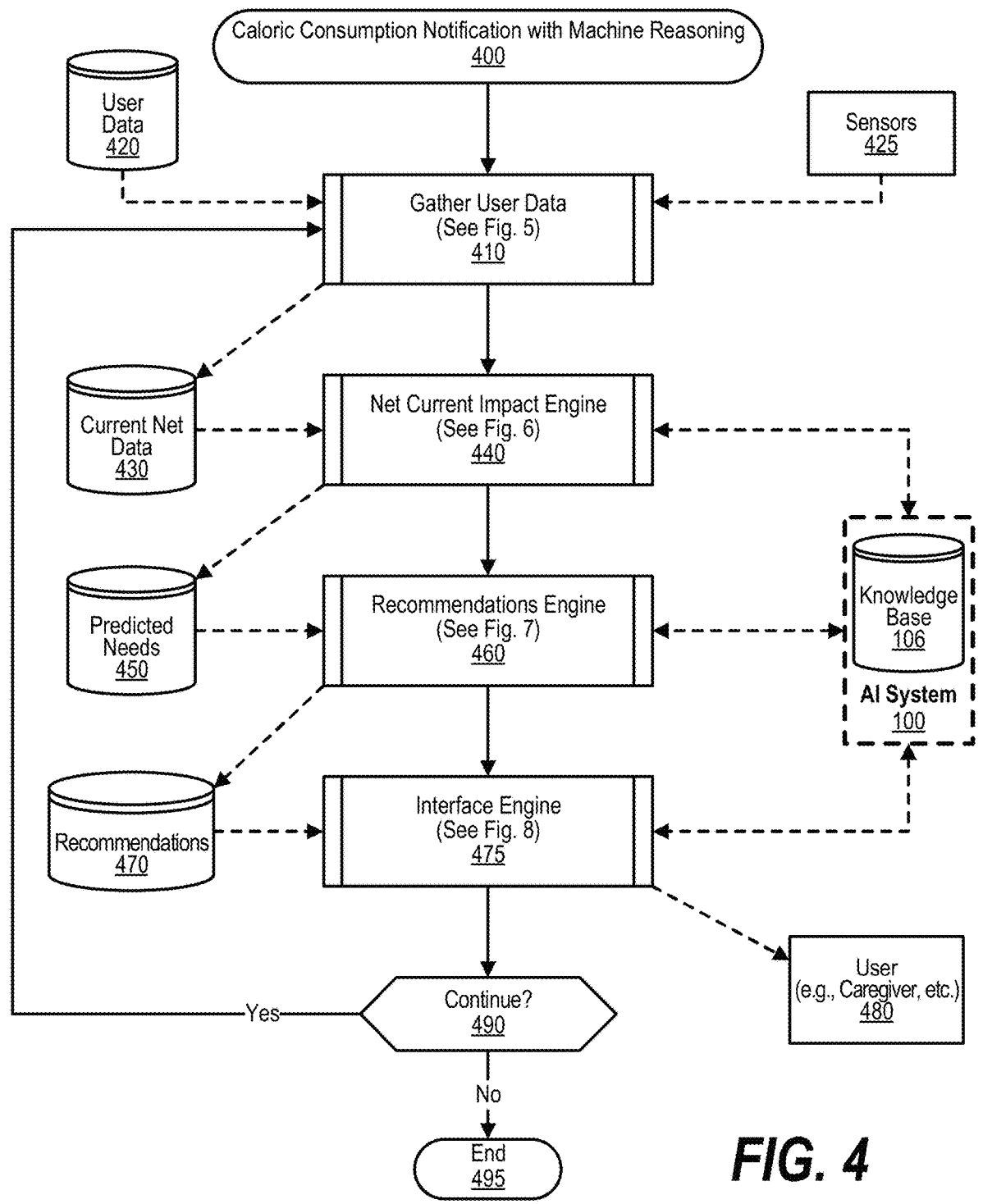
FIG. 4 is a depiction of a high-level flowchart showing overall logic used to provide channel calorie consumption and notification using machine reasoning.

FIG. 4 is a depiction of a high-level flowchart showing overall logic used to provide channel calorie consumption and notification using machine reasoning. FIG. 4 processing commences at 400 and shows the high-level steps taken by a process that performs caloric consumption notification using machine reasoning, such as Artificial Intelligence (AI). At predefined process 410, the process performs the Gather User Data routine (see FIG. 5 and corresponding text for processing details). This routine receives user data 420 (human subject data) from a data store, as well as environmental and other human subject data from various sensors 425. The routine provides current net data 430 for the human subject which is stored in a data store.

Figure 6:
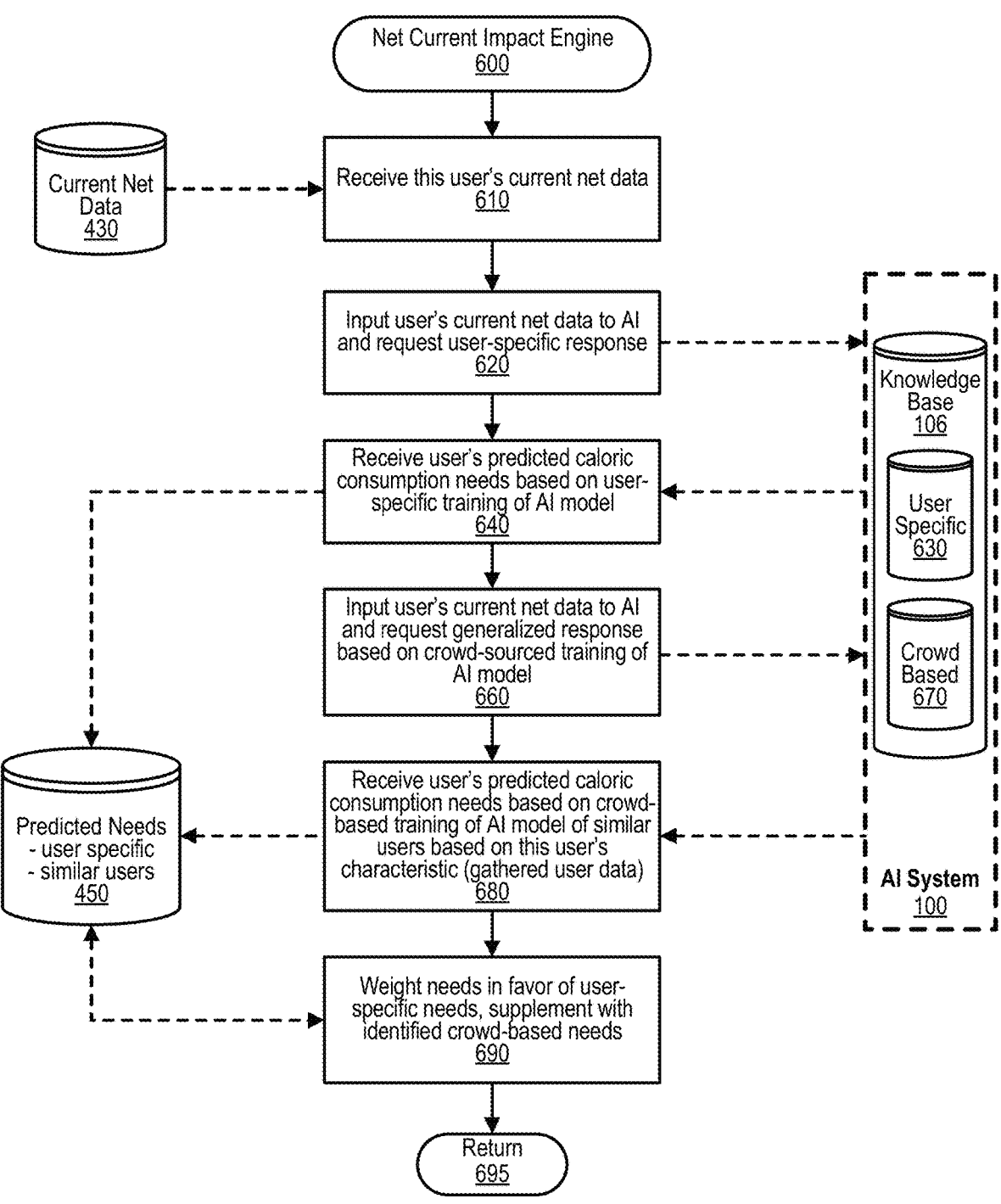
FIG. 6 is a depiction of a flowchart showing the logic used to determine a current net impact used to provide dietary recommendations.

At predefined process 440, the process performs the Net Current Impact Engine routine (see FIG. 6 and corresponding text for processing details). This routine receives the human subject's current net data 430 from a data store, as well as data from AI system 100. The routine results in a set of the human subject's predicted needs (caloric needs, nutrition needs, etc.) that are stored in data store 450.

Figure 7:
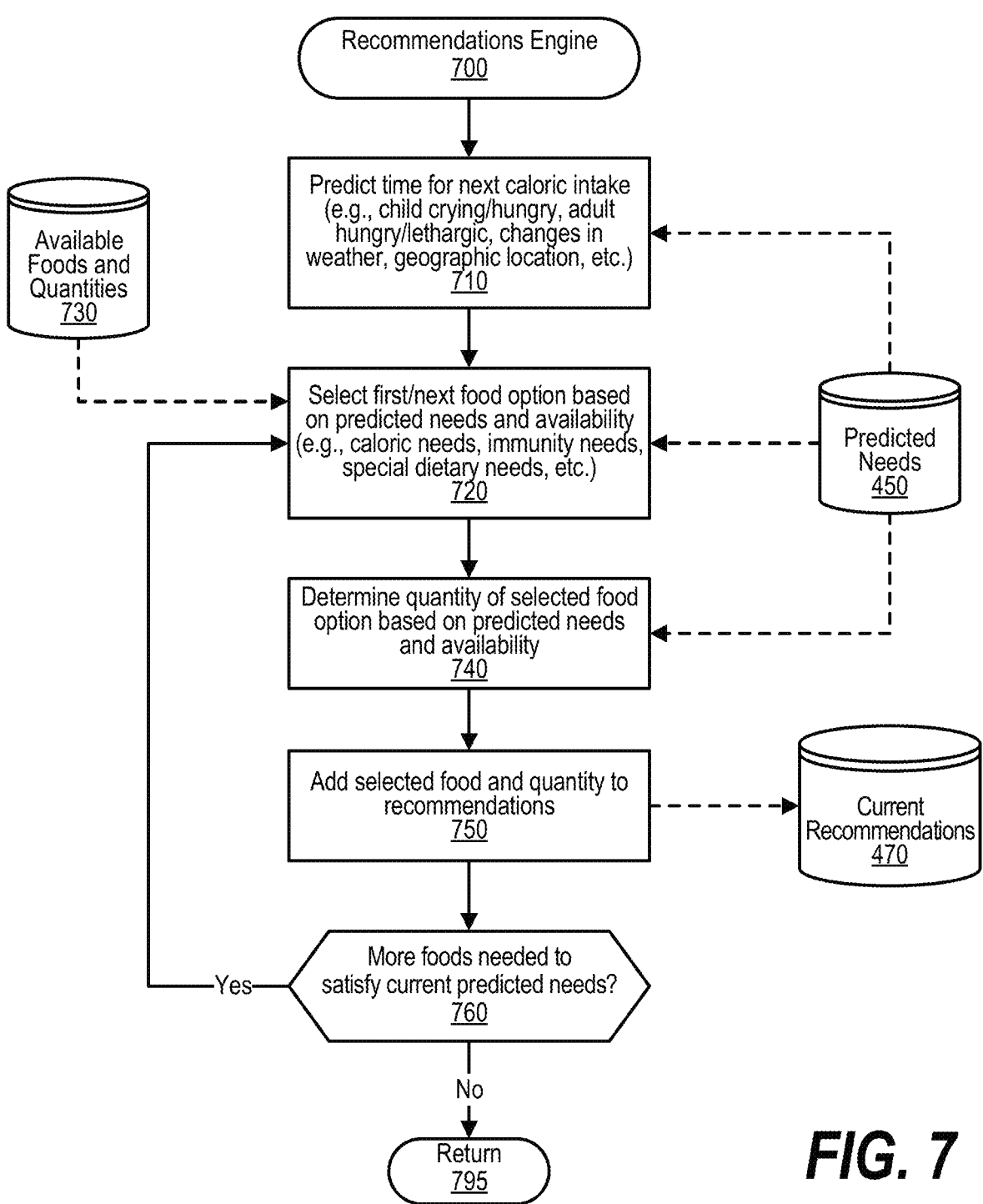
FIG. 7 is a depiction of a flowchart showing the logic used to provide dietary recommendation pertaining to a human subject to a user of the system, such as a caretaker.

At predefined process 460, the process performs the Recommendations Engine routine (see FIG. 7 and corresponding text for processing details). This routine receives the human subject's predicted needs from data store 450 as well as data learned by AI system 100 and stored in corpus 106 which is used to predict the human subject's needs and formulate recommendations. The result of predefined process 460 are recommendations, such as a meal time and meal details, recommended for the human subject which are stored in data store 470.

Figure 8:
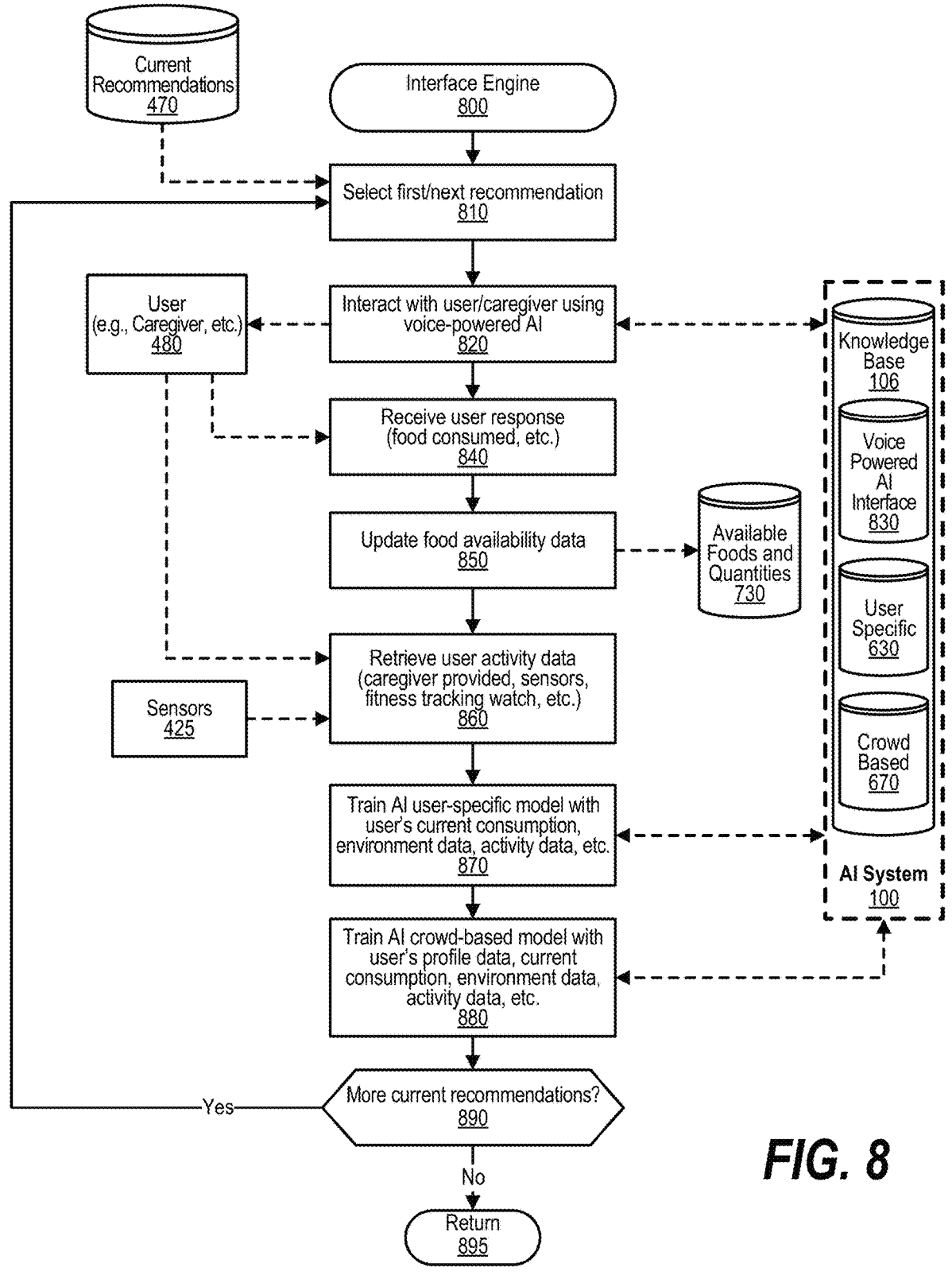
FIG. 8 is a depiction of a flowchart showing the logic used by an interface engine to interface with the human subject and the user to gather data pertaining to the dietary needs of the human subject.

At predefined process 475, the process performs the Interface Engine routine (see FIG. 8 and corresponding text for processing details). This routine uses a virtual assistant to interface between the AI system and the user, such as the human subject or a caretaker for the human subject. This routine receives recommendations from data store 470 and uses the virtual assistant technology to provide to user 480 (e.g., verbal instructions played through a speaker to the user (caretaker) with the virtual assistant receiving verbal replies from the user that are input to the AI system, etc.).

The process determines as to whether continue the process or terminate (decision 490). If the process continues, then decision 490 branches to the 'yes' branch which loops back to predefined process 410 to continue the process as described above. This looping continues until the process terminates, at which point decision 490 branches to the 'no' branch exiting the loop. FIG. 4 processing thereafter ends at 495.

Figure 5:
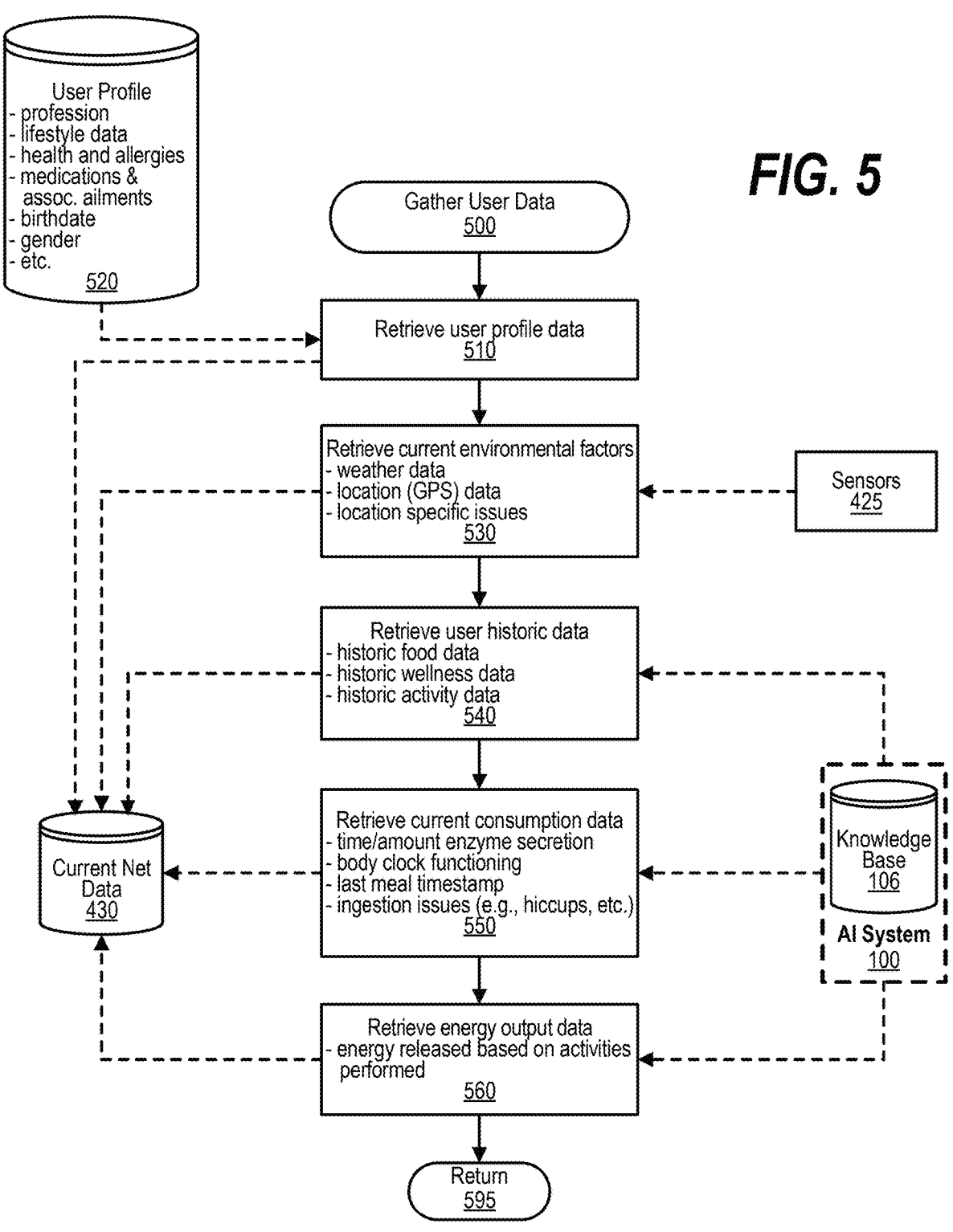
FIG. 5 is a depiction of a flowchart showing the logic used to gather data pertaining to a human subject of the channel calorie consumption and notification system.

FIG. 5 is a depiction of a flowchart showing the logic used to gather data pertaining to a human subject of the channel calorie consumption and notification system. FIG. 5 processing commences at 500 and shows the steps taken by a process that gathers user data. At step 510, the process retrieves user profile data from data store 520. This data includes data about the human subject such as the human subject's profession, lifestyle data, health and allergies data, medications and associated ailments, as well as the human subject's birthdate and gender. This profile data is fed into Current Net Data 430 that is stored in a data store.

At step 530, the process retrieves current environmental factors such as weather data location (GPS) data and any location specific issues data from sensors 425. This current environmental factors data is fed into Current Net Data 430 that is stored in a data store. At step 540, the process retrieves the human subject's historic data such as historic food data, historic wellness data, and historic activity data from AI system 100 that has the data stored in corpus 106. This historic data pertaining to the human subject is fed into Current Net Data 430 that is stored in a data store.

At step 550, the process retrieves current consumption data pertaining to the human subject. The current consumption data includes the time and amount of enzyme secretion, the human subject's body clock functioning, the human subject's last meal data and timestamp, and any ingestion issues (e.g., hiccups, etc.) pertaining to the human subject. This current consumption data pertaining to the human subject is fed into Current Net Data 430 that is stored in a data store.

At step 560, the process retrieves the human subject's current energy output data, such as energy that has been released based on activities performed by the human subject. This data is retrieved from sensors 425 as well as from data gathered from the human subject the user (caretaker, etc.) or others and provided to AI system 100. This energy output data pertaining to the human subject is fed into Current Net Data 430 that is stored in a data store. FIG. 5 processing thereafter returns to the calling routine (see FIG. 4) at 595.

FIG. 6 is a depiction of a flowchart showing the logic used to determine a current net impact used to provide dietary recommendations. FIG. 6 processing commences at 600 and shows the steps taken by a process that is performed by the Net Current Impact Engine. At step 610, the process receives this human subject's current net data 430 from a data store.

At step 620, the process inputs the human subject's current net data to AI system 100 and requests a human subject-specific response from the AI system. In one embodiment, as shown, knowledge base, or corpus 106, utilized by AI system 100 includes both human subject specific data that is stored in data store 630 within the corpus as well as crowd based data that is gathered from other individuals utilizing the system with such data being stored in data store 670 within corpus 106 that is managed by AI system 100. At step 640, the process receives the human subject's predicted caloric consumption needs based on the human subject-specific training of the AI model being executed by AI system 100. This set of predicted data is stored in predicted needs data store 450.

At step 660, the process inputs the human subject's current net data to AI system 100 and requests generalized response data that is based on the crowd-sourced training of the AI model. At step 680, the process receives the human subject's predicted caloric consumption needs based on the crowd-based training of AI model of similar individuals with the prediction based on the human subject's specific characteristic found in the gathered user data. This set of predicted data is also stored in predicted needs data store 450.

At step 690, the process weighs the human subject's caloric needs in favor of the human subject-specific needs found in data store 450 and supplements the needs with any identified crowd-based needs that were stored in data store 450. FIG. 6 processing thereafter returns to the calling routine (see FIG. 4) at 695.

FIG. 7 is a depiction of a flowchart showing the logic used to provide dietary recommendation pertaining to a human subject to a user of the system, such as a caretaker. FIG. 7 processing commences at 700 and shows the steps taken by a process that performs the Recommendations Engine.

At step 710, the process predicts a time for the next caloric intake by the human subject. This can be based on historic predicted needs as well as other factors such as a child that is crying or exhibiting signs of hunger, an adult human subject that is hungry or lethargic, changes in weather, the human subject's geographic location, and the like. This predicted needs data is retrieved from data store 450.

At step 720, the process selects the first food option based on the human subject's predicted needs and food availability, such as the caloric needs of the human subject, the human subject's immunity needs, the human subject's special dietary needs, and the like. Available foods and quantities are retrieved from data store 730 and the predicted needs data of the human subject are retrieved from data store 450.

At step 740, the process determines the quantity of the selected food option based on the predicted needs and the quantity of the selected food that is available. At step 750, the process adds the selected food and the determined quantity to the current set of recommendations that are stored in data store 470.

The process determines as to whether more foods are needed to satisfy the current predicted needs of the human subject (decision 760). If more foods are needed to satisfy the current predicted needs of the human subject, then decision 760 branches to the 'yes' branch which loops back to step 720 to select the next food needed for the meal. This looping continues until no more foods are needed, at which point decision 760 branches to the 'no' branch exiting the loop. FIG. 7 processing thereafter returns to the calling routine (see FIG. 4) at 795.

FIG. 8 is a depiction of a flowchart showing the logic used by an interface engine to interface with the human subject and the user to gather data pertaining to the dietary needs of the human subject. FIG. 8 processing commences at 800 and shows the steps taken by a process that performs an Interface Engine by a virtual assistant. At step 810, the process selects the first recommendation from data store 470.

At step 820, the process interacts with user 480, such as a caregiver or the human subject, using a voice-powered AI that is provided by Voice Powered AI Interface 830 component of AI system 100. At step 840, the process receives a response from user 480, such as food that was consumed, and the like. At step 850, the process updates food availability data based on the food and amount that was consumed by the human subject. The updated food quantities are stored in data store 730.

At step 860, the process retrieves the human subject's activity data. This data can be provided by the user or caregiver 480, retrieved from sensors 425, such as a fitness tracking watch, and the like. At step 870, the process trains AI system 100's human subject-specific model with the human subject's current consumption, the current environment data, the human subject's activity data, and the like. This results in training of user specific model 630 that is maintained by AI system 100.

At step 880, the process trains AI crowd-based model 670 with the human subject's profile data, the human subject's current consumption, and the current environment data, activity data. The process determines whether there are any more current recommendations to process (decision 890). If there are more current recommendations to process, then decision 890 branches to the 'yes' branch which loops back to step 810 to select and process the next recommendation using the interface engine as described above. This looping continues until there are no more recommendations to process, at which point decision 890 branches to the 'no' branch exiting the loop. FIG. 8 processing thereafter returns to the calling routine (see FIG. 4) at 895.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While particular embodiments have been shown and described, it will be obvious to those skilled in the art that, based upon the teachings herein, that changes and modifications may be made without departing from this invention and its broader aspects. Therefore, the appended claims are to encompass within their scope all such changes and modifications as are within the true spirit and scope of this invention. Furthermore, it is to be understood that the invention is solely defined by the appended claims. It will be understood by those with skill in the art that if a specific number of an introduced claim element is intended, such intent will be explicitly recited in the claim, and in the absence of such recitation no such limitation is present. For non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to inventions containing only one such element, even when the same claim includes the introductory phrases "one or more" or "at least one" and indefinite articles such as "a" or "an"; the same holds true for the use in the claims of definite articles.

What is claimed is:

1. A computer-implemented method for a personalized virtual assistant interface implemented by an information handling system that includes a processor and a memory, the method comprising:

training an artificial intelligence (AI) system to generate a meal recommendation corresponding to a human subject, the AI system trained with a plurality of eating characteristics corresponding to the human subject, wherein the eating characteristics include one or more eating patterns, a plurality of health data, and a plurality of activity data;

communicating with a plurality of sensors to obtain current food consumption data and current physical activity data for the human subject to include in a feedback loop;

continually training the AI system using the feedback loop to generate the meal recommendation based on the current food consumption data and current physical activity data;

determining a set of caloric needs pertaining to the human subject using current net data for the human subject, the current net data including current consumption data and current energy output data for the human subject provided by one or more sensors;

generating, by the trained AI system, the meal recommendation corresponding to the human subject, wherein the meal recommendation includes a recommended meal time and one or more food recommendations that are based upon the set of caloric needs pertaining to the human subject; and automatically providing the generated meal recommendation at a time that is based on the recommended meal time at the personalized virtual assistant interface that is voice-enabled and is accessible by the AI system.

2. The method of claim 1 further comprising:

inputting a set of personal characteristics corresponding to the human subject to the trained AI system;

responsively receiving, from the trained AI system, a crowd-based caloric needs data based on a comparison of the human subject's personal characteristics with a plurality of personal characteristics corresponding to a plurality of other human subjects with sets of corresponding dietary data and the plurality personal characteristics previously learned by the AI system; and generating the meal recommendation by further incorporating the received crowd-based caloric needs data.

3. The method of claim 1 further comprising:

receiving a plurality of environmental factors corresponding to a current location of the human subject, wherein at least one of the environmental factors is a set of weather data of the current location, wherein the generating of the meal recommendation is further based on at least one of the received environmental factors.

4. The method of claim 1 further comprising:

identifying, using one or more sensors, a plurality of food items currently available to a user, wherein the generation of the meal recommendation is further based on the food items currently available to the user; and updating the plurality of currently available food items based on a usage of the available food items performed by the user.

5. The method of claim 1 further comprising:

vocally interacting with a user using the voice-enabled virtual assistant, wherein a user provides one or more current individual attributes pertaining to the human subject; and further training the AI system using the current individual attributes, wherein the user is a caretaker of the human subject.

6. An information handling system for a personalized virtual assistant interface comprising:

one or more processors;

a memory coupled to at least one of the processors;

a set of computer program instructions stored in the memory and executed by at least one of the processors in order to perform actions comprising:

training an artificial intelligence (AI) system to generate a meal recommendation corresponding to a human subject, the AI system trained with a plurality of eating characteristics corresponding to a human subject, wherein the eating characteristics include one or more eating patterns, a plurality of health data, and a plurality of activity data;

communicating with a plurality of sensors to obtain current food consumption data and current physical activity data for the human subject to include in a feedback loop;

continually training the AI system using the feedback loop to generate the meal recommendation based on the current food consumption data and current physical activity data;

determining a set of caloric needs pertaining to the human subject using current net data for the human subject, the current net data including current consumption data and current energy output data for the human subject provided by one or more sensors;

generating, by the trained AI system, the meal recommendation corresponding to the human subject, wherein the meal recommendation includes a recommended meal time and one or more food recommendations that are based upon the set of caloric needs pertaining to the human subject; and automatically providing the generated meal recommendation at a time that is based on the recommended meal time at the personalized virtual assistant interface that is voice-enabled and is accessible by the AI system.

7. The information handling system of claim 6 wherein the actions further comprise:

inputting a set of personal characteristics corresponding to the human subject to the trained AI system;

responsively receiving, from the trained AI system, a crowd-based caloric needs data based on a comparison of the human subject's personal characteristics with a plurality of personal characteristics corresponding to a plurality of other human subjects with sets of corresponding dietary data and the plurality personal characteristics previously learned by the AI system; and generating the meal recommendation by further incorporating the received crowd-based caloric needs data.

8. The information handling system of claim 6 wherein the actions further comprise:

receiving a plurality of environmental factors corresponding to a current location of the human subject, wherein at least one of the environmental factors is a set of weather data of the current location, wherein the generating of the meal recommendation is further based on at least one of the received environmental factors.

9. The information handling system of claim 6 wherein the actions further comprise:

identifying, using one or more sensors, a plurality of food items currently available to a user, wherein the generation of the meal recommendation is further based on the food items currently available to the user; and updating the plurality of currently available food items based on a usage of the available food items performed by the user.

10. The information handling system of claim 6 wherein the actions further comprise:

vocally interacting with a user using the voice-enabled virtual assistant, wherein the user provides one or more current individual attributes pertaining to the human subject; and further training the AI system using the current individual attributes, wherein the user is a caretaker of the human subject.

11. A computer program product stored in a computer readable storage medium, comprising computer program code that, when executed by an information handling system, performs actions comprising:

training an artificial intelligence (AI) system to generate a meal recommendation corresponding to a human subject, the AI system trained with a plurality of eating characteristics corresponding to a human subject, wherein the eating characteristics include one or more eating patterns, a plurality of health data, and a plurality of activity data;

communicating with a plurality of sensors to obtain current food consumption data and current physical activity data for the human subject to include in a feedback loop;

continually training the AI system using the feedback loop to generate the meal recommendation based on the current food consumption data and current physical activity data;

determining a set of caloric needs pertaining to the human subject using current net data for the human subject, the current net data including current consumption data and current energy output data for the human subject provided by one or more sensors;

generating, by the trained AI system, the meal recommendation corresponding to the human subject, wherein the meal recommendation includes a recommended meal time and one or more food recommendations that are based upon the set of caloric needs pertaining to the human subject; and automatically providing the generated meal recommendation at a time that is based on the recommended meal time at a personalized virtual assistant interface that is voice-enabled and is accessible by the AI system.

12. The computer program product of claim 11 wherein the actions further comprise:

inputting a set of personal characteristics corresponding to the human subject to the trained AI system;

responsively receiving, from the trained AI system, a crowd-based caloric needs data based on a comparison of the human subject's personal characteristics with a plurality of personal characteristics corresponding to a plurality of other human subjects with sets of corresponding dietary data and the plurality personal characteristics previously learned by the AI system; and generating the meal recommendation by further incorporating the received crowd-based caloric needs data.

13. The computer program product of claim 11 wherein the actions further comprise:

receiving a plurality of environmental factors corresponding to a current location of the human subject, wherein at least one of the environmental factors is a set of weather data of the current location, wherein the generating of the meal recommendation is further based on at least one of the received environmental factors.

14. The computer program product of claim 11 wherein the actions further comprise:

identifying, using one or more sensors, a plurality of food items currently available to a user, wherein the generation of the meal recommendation is further based on the food items currently available to the user; and updating the plurality of currently available food items based on a usage of the available food items performed by the user.

* * * * *